US010520721B2

(12) United States Patent
Nowatzyk (10) Patent No.: US 10,520,721 B2
(45) Date of Patent: Dec. 31, 2019

(54) OPTICAL BEAM SCANNING SYSTEM HAVING A SYNTHETIC CENTER OF BEAM ROTATION (71) Applicant: THE BRAIN WINDOW, INC., Sherman Oaks, CA (US)

(72) Inventor: Andreas G. Nowatzyk, San Jose, CA (US)

(73) Assignee: THE BRAIN WINDOW, INC., Sherman Oaks, CA (US)

(*) Notice: Subject to any disclaimer, the term of this patent is extended or adjusted under 35 U.S.C. 154(b) by 0 days.

(21) Appl. No.: 14/466,823

(22) Filed: Aug. 22, 2014

(65) Prior Publication Data
US 2015/0168713 A1 Jun. 18, 2015

Related U.S. Application Data (60) Provisional application No. 61/872,455, filed on Aug. 30, 2013.

(51) Int. Cl.
G02B 26/08 (2006.01)
G02B 26/10 (2006.01)
A61B 3/10 (2006.01)

(52) U.S. Cl.
CPC ............ *G02B 26/0816* (2013.01); *A61B 3/10* (2013.01); *A61B 3/1025* (2013.01); *G02B 26/101* (2013.01); *G02B 26/105* (2013.01)

(58) Field of Classification Search
CPC .... G02B 26/00; G02B 26/08; G02B 26/0816; G02B 26/10; G02B 26/101; G02B 26/105
USPC ......... 359/196.1, 197.1, 198.1, 200.7, 201.1, 359/201.2, 202.1, 212.1, 849, 857, 861
See application file for complete search history.

(56) References Cited

U.S. PATENT DOCUMENTS

| 9,039,188 | B2* | 5/2015 | Takanokura | G03B 21/14 353/31 |
| 2005/0264502 | A1* | 12/2005 | Sprague | G02B 5/10 345/84 |
| 2009/0051935 | A1* | 2/2009 | Cooper | B23K 26/041 356/616 |
| 2009/0109561 | A1* | 4/2009 | Cook | G02B 7/1821 359/861 |

(Continued)

OTHER PUBLICATIONS

E.J. Galvez and P.M. Koch, "Use of four mirrors to rotate linear polarization but preserve input-output collinearity. II." 1997 Optical Society of America.

(Continued)

*Primary Examiner* — William R Alexander
(74) *Attorney, Agent, or Firm* — Arent Fox LLP (57) ABSTRACT An optical beam scanning system having a synthetic center of beam rotation. A front, primary intermediate and back mirrors having respective motors are provided to receive and redirect an optical beam. A controller is connected to orient the front, primary intermediate and back mirrors so that a beam received by the front mirror from a given direction is directed toward the primary intermediate mirror, by the primary intermediate mirror toward the back mirror, and by the back mirror so as to pass through a selected point spaced apart from the back mirror in one of a plurality of selectable different directions. A secondary intermediate mirror may be provided so as to receive the beam from the primary intermediate mirror and redirect it toward the back mirror. The beam may be directed thereby through a synthetic center of beam rotation.

12 Claims, 5 Drawing Sheets (56) References Cited

U.S. PATENT DOCUMENTS

2013/0169940 A1* 7/2013 Takanokura .......... G03B 21/14
353/31

* cited by examiner

OPTICAL BEAM SCANNING SYSTEM HAVING A SYNTHETIC CENTER OF BEAM ROTATION

CROSS REFERENCE TO RELATED APPLICATIONS

Applicant hereby claims the benefit of U.S. patent application Ser. No. 14/216,708, filed Mar. 17, 2014, which claimed the benefit of U.S. Provisional Patent Application No. 61/852,458, filed Mar. 15, 2013; and of U.S. Provisional Patent Application No. 61/872,455, filed Aug. 20, 2013, all of which are hereby incorporated by reference in their entirety.

FIELD OF THE INVENTION

This invention relates to methods and systems for scanning a light beam in a selected direction, and particularly to a method and system for scanning a light beam in a selected direction through a selected center of rotation of the beam that is spatially separated from the scanning optics, referred to herein as a synthetic center of beam rotation, or "SCBR."

BACKGROUND

There are many situations where it is desirable to be able to scan a light beam in a particular direction. For example, a two-dimensional image of an object may be generated by scanning a light beam in two dimensions and capturing resulting light emanating from the object, e.g., reflected by a fluorescent light, with a point detector whose output is synchronized with the scanning light beam to produce image data. This technique can also be extended to three dimensions. A particular case of this is confocal imaging, where a scanning light beam has a focal point that is optically conjugate with a pinhole spatial filter in front of the detector, which serves to reduce the image noise from scattered light.

One known way to scan a light beam is to use a pair of mirrors mounted on respective galvanometers so that the axis of rotation of each galvanometer lies in the plane of its respective mirror and they are disposed askew, typically perpendicular, to one another such that a light beam from a light source strikes and is reflected off a first mirror toward a second mirror, where it is reflected from the second mirror in the ultimate desired direction.

For good performance, galvanometric scanners need to be used with and closely matched to other optics included in a scanning system. The critical component of the system typically is a scan lens that forms the input optic and translates the angular deflection of the scan beam by the rotating mirrors mounted on galvanometers into a linearly moving point in the plan of a virtual image, while at the same time illuminating the full back-aperture of an objective lens that forms the output optic. This is a difficult design problem that is compounded by the fact that each galvanometer has its own pivot point at a different distance from the virtual image plane, which typically necessitates the use of relay optics between each galvanometer. Not only does the design and production of a good scan lens exceed the capabilities of most laboratories, but the scan lens is also very specific to the objective or other "front end" optical device for which the system is designed and may be limited to just one type of optical device, such as, for example, a microscope, an endoscope or an opthalmoscope.

It would be desirable to have a beam scanning method and system that may be used with a variety of front end optical devices and does not require complicated lens design.

Generally, there are applications for optical beam scanners where locating the center of rotation of the beam in free space away from any mirror or structure would be advantageous. In conventional beam steering designs that is not possible. The rotation of a beam typically occurs at fold mirror face and the pivot point is located on the mirror face coincident with the axis of rotation of the mirror.

It would also be desirable to have a beam scanning method and system that produces a scanning beam whose center of rotation is located in free space away from any mirror or structure.

SUMMARY

Accordingly, one aspect of the disclosure of this application provides a front mirror having a motor to orient the front mirror relative to a frame of reference so as to receive and redirect and optical beam in accordance with the orientation of the front mirror; a primary intermediate mirror having a motor to orient the primary intermediate mirror relative to the frame of reference so as to receive and redirect the optical beam in accordance with the orientation of the primary intermediate mirror; and a back mirror having a motor to orient the back mirror relative to the frame of reference so as to receive and redirect the optical beam in accordance with the orientation of the back mirror. A controller is connected to the front, primary intermediate and back mirrors to orient the front, primary intermediate and back mirrors so that a beam received by the front mirror from a given direction is directed toward the primary intermediate mirror, and is directed by the primary intermediate mirror toward the back mirror, and is redirected by the back mirror so as to pass through a selected point spaced apart from the back mirror in one of a plurality of selectable different directions.

In another aspect of the disclosure, a secondary intermediate mirror is provided, having a motor to orient the secondary intermediate mirror relative to the frame of reference so as to receive and redirect the optical beam in accordance with the orientation of the second intermediate mirror in response to the controller. The second intermediate mirror is disposed between the primary intermediate mirror and the back mirror so as to receive the beam from the primary intermediate mirror and redirect it toward the back mirror. The beam is redirected by the primary intermediate mirror toward the back mirror through the secondary intermediate mirror.

A method for controlling an optical beam is also disclosed wherein at least three mirrors are arranged so as to have respective axes of rotation parallel to the respective mirror surfaces. The mirrors are rotated so that the beam is redirected by a first of the mirrors to a second of the mirrors, by the second of the mirrors to a third of the mirrors, and by the third of the mirrors in a selected direction through a selected point spaced from the mirror surfaces. A fourth mirror may be arranged to redirect the beam from the second mirror to the third mirror.

It is to be understood that this summary is provided as a means for generally determining what follows in the drawings and detailed description, and is not intended to limit the scope of the invention. The foregoing and other objects, features, and advantages of the invention will be readily

DETAILED DESCRIPTION OF EXAMPLE EMBODIMENTS

The methods and systems described hereafter overcome the need for a scan lens in a light beam scanning system by producing a center of rotation of an input beam, or an output beam, or both, that is spatially separated from the scanning optics, that is, a synthetic center of beam rotation (SCBR). By analogy to ray optics theory, the center of rotation of the input or output beam may be compared to a focal point whose conjugate is at infinity, or is another focal point, except that ordinarily the width of the beam may not be considered infinitesimal and may have to be taken into account in an optical system employing the methods and systems disclosed herein.

In scanning a surface that is flat, for example, it is ordinarily desirable for the focal point of the scan beam to be at the flat surface regardless of lateral position. It is also often desirable for the path of the scan beam to be normal to the flat surface where it meets the flat surface. An appropriately designed scan lens system can provide either or both of these characteristics, but with complexity, limited flexibility and significant expense.

Using the methods and systems disclosed herein, the scan lens can be eliminated. For example, by providing a beam scanner according to the novel disclosure herein having an input beam along a fixed trajectory and an output beam whose SCBR is placed at the front focal point of a standard objective lens, the rotation of the beam about that point will cause the beam to exit the back side of the objective and scan laterally parallel to a fixed axis, which may be made to be the optical axis of the objective.

A scanner according to the present invention may also be uses to pass a cone shaped array of light beams through a small aperture, such as the pupil of a human eye. Thus, as another example, to scan the retina of a human eye, the SCBR may be placed at the center of curvature, or at one or more of a locus of points representing the differential centers of curvature of the retina, which lie inside the eye itself.

Other examples of use of the methods and systems disclosed herein may be known or found and used, without departing from the principles of the invention.

1. Three Mirror Embodiment

Figure 1:
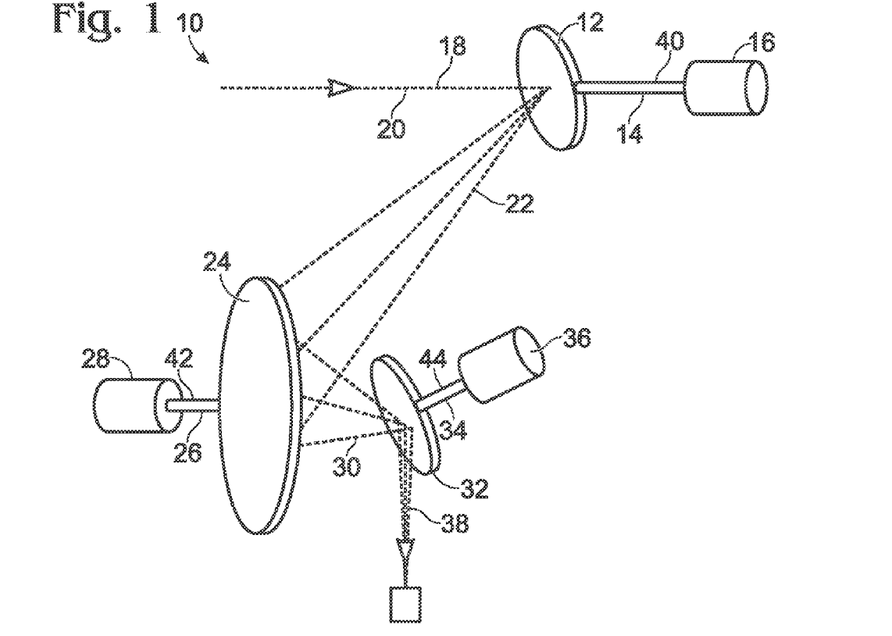
FIG. 1 is a perspective of a three-mirror scanning system including respective galvanometers to rotate the mirrors according to the present invention.

One way to avoid the need for a scan lens according to a basic principal of the invention is to use three scan mirrors in a scanning system 10 wherein the rotation of each of the three mirrors is controlled by a respective precision galvanometer, as shown in FIG. 1. First scan mirror 12, which rotates about axis 14 under control of galvanometer 16, receives a light beam 18 from a light source, such as a laser, along an input path 20 and reflects the light beam along a first reflection path 22 determined by the angle of incidence that the input path makes with the first scan mirror 12. Second scan mirror 24, which rotates about axis 26 under control of galvanometer 28, receives the light beam along the first reflection path 22 and reflects the beam along a second reflection path 30 determined by the angle of incidence that the first reflection path makes with the second scan mirror 24. Third scan mirror 32, which rotates about axis 34 under control of galvanometer 36, receives the light beam along the second reflection path 30 and reflects the beam along a third, output reflection path 38 determined by the angle of incidence that the second reflection path makes with the third scan mirror 32. The light beam is thereby controlled to scan in a desired direction at the output of the scanner.

Depending on the application of this embodiment, the first mirror 12, the second mirror 24, and the third mirror 32 may also be referred to together as the "front mirror," the "intermediate mirror" or "primary intermediate mirror," and the "back mirror," respectively; or conversely together as the "back mirror," the "intermediate mirror" or "primary intermediate mirror," and the "front mirror," respectively.

Ordinarily, each mirror 12, 24 and 32 would comprise a planar reflective surface and be attached to a respective galvanometer shaft 40, 42 and 44 so that the center of rotation of each mirror lies essentially in the plane of the reflecting surface of the mirror. However, it is to be understood that spherical, aspherical or other types of mirrors might be used instead of a plane mirror, and that all or a portion of the reflective surface of one or more of the mirrors might be offset from the axis of rotation without departing from the principles of the invention.

2. Four Mirror Embodiment

Figure 2:
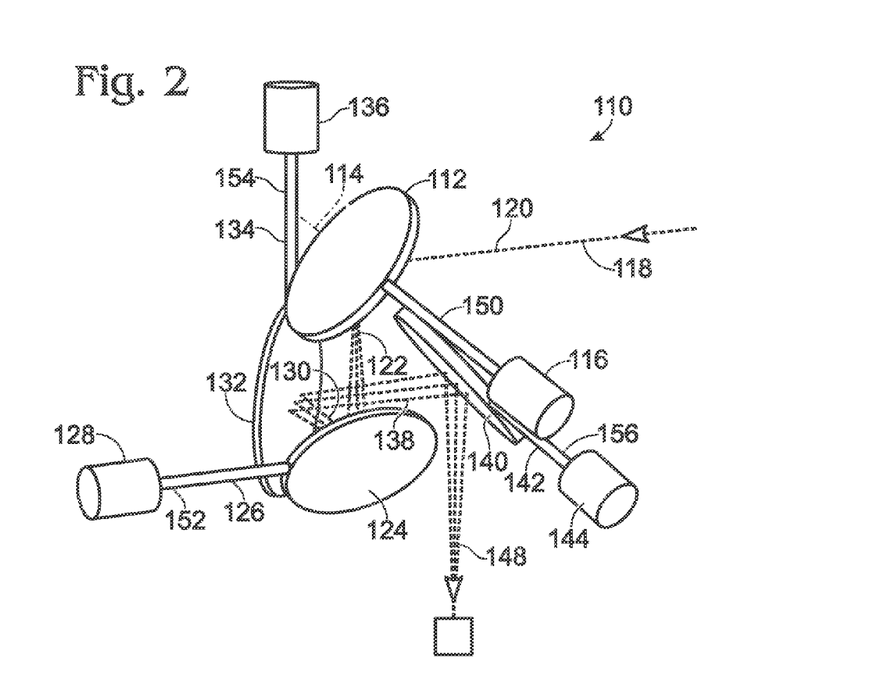
FIG. 2 is a perspective of a four-mirror scanning system including respective galvanometers to rotate the mirrors according to the present invention.

A second embodiment 110 of a scanning system according to the invention that avoids the need for a scan lens uses four mirrors wherein the rotation of each of the four mirrors is controlled by a respective galvanometer, as shown in FIG. 2. In this embodiment first scan mirror 112, which rotates about axis 114 under control of galvanometer 116, receives a light beam 118 from a light source, such as a laser, along an input path 120 and reflects the light beam along a first reflection path 122 determined by the angle of incidence that the input path makes with the first scan mirror 112. Second scan mirror 124, which rotates about axis 126 under control of galvanometer 128, receives the light beam along the first reflection path 122 and reflects the beam along a second reflection path 130 determined by the angle of incidence that the first reflection path makes with the second scan mirror 124. Third scan mirror 132, which rotates about axis 134 under control of galvanometer 136, receives the light beam along the second reflection path 130 and reflects the beam along a third reflection path 138 determined by the angle of incidence that the second reflection path makes with the third scan mirror 132. Fourth scan mirror 140, which rotates about axis 142 under control of galvanometer 144, receives the light beam along the third reflection path 146 and reflects the beam along a fourth, output reflection path 148 determined by the angle of incidence that the third reflection path makes with the fourth scan mirror 140. The light beam is thereby controlled to scan in a desired direction at the output of the scanner.

Depending on the application of this embodiment, the first mirror 112, the second mirror 124, the third mirror 132, and the fourth mirror 140 may also be referred to together as the "front mirror," the "primary intermediate mirror," the "secondary intermediate mirror," and the "back mirror," respectively; or conversely together as the "back mirror," the "secondary intermediate mirror," the "primary intermediate mirror," and the "front mirror," respectively.

As with the three-mirror scanner embodiment 10, each mirror 112,124, 132 and 140 would comprise a planar reflective surface and be attached to a respective galvanometer shaft 150, 152, 154 and 156 so that the center of rotation of each mirror lies essentially in the plane of the reflecting surface of the mirror. However, it is to be understood that spherical, aspherical or other types of mirrors might be used instead of a plane mirror, and that all or a portion of the reflective surface of one or more of the mirrors might be offset from the axis of rotation without departing from the principles of the invention.

3. Synthetic Center of Beam Rotation

In the both the three mirror and four mirror system the galvanometer-controlled mirrors may be arranged and controlled so that the output beam rotates about a SCBR not located at the surface of any of the mirrors. The four mirror system provides the advantages that the orthogonal axes permit tighter packing of the mirror and galvanometer components and the angles of incidence and reflection of beams are smaller so that the distortion of a real beam spot that makes the spot elliptical rather than circular and makes the energy cross section non-uniform is minimized.

To generate an SCBR the mirror rotation angles about their rotation axes must be single-valued functions of the position of the SCBR and the direction of each beam passing through the SCBR for a given set of angles between the mirror rotation axes; that is, there are no redundant combinations of those rotation angles. The rotation angles are preferably determined by a digital computer that solves for the required mirror rotation angles based on the desired SCBR, or pairs of SCBRs in the case of a dual SCBR system as discussed below. The computer provides that information to a controller, or is programmed as a controller, to control the galvanometers to set those mirror angles.

In the particular case of a four mirror, single SCBR system, for all the solutions of the four mirror positions resulting in a SCBR, the beam reflects off the first scan mirror 112 at a single point, so the mirror can be relatively small, the beam size being the principal constraint. Also, all beams emerging from the SCBR reflect of the second mirror 124 along a single line which is, ideally, collinear with the axis of rotation of that mirror. Consequently, that mirror may be relatively narrow. The sizes of the third scan mirror 132 and fourth scan mirror 140 depend on both the beam size and the sizes of the ellipses traced on those mirrors by rotating the center of the beam around the nominal trajectory from the SCBR to the four scan mirror the maximum cone angle.

4. Geometric and Mathematical Models of Quad Galvo-Controlled Scan Mirrors

Figure 3:
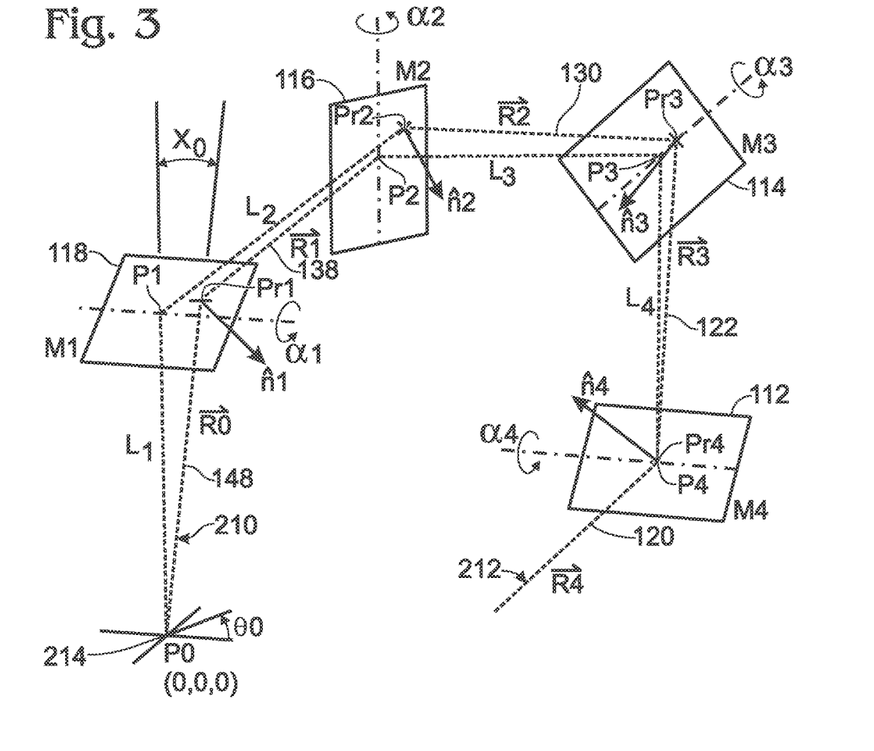
FIG. 3 is geometric representation of a mathematical model of a four-mirror scanning system according to the present invention.

A geometric model 200 of the paths of a light beam travelling through a four galvo-controlled mirror ("quad") scanner is shown in FIG. 3. A functional mathematical model of this system based on linear algebra and MathCAD 15® code is shown in Appendix A.

In FIG. 3, the first scan mirror 112 is denoted $M_4$ for the purpose of the functional mathematical model. Similarly, the second scan mirror 114 is denoted $M_3$, the third scan mirror 116 is denoted $M_2$, and the fourth scan mirror 118 is denoted $M_1$. This is because the mathematical model is a linear algebra model that progresses from the output 210 to the input 212 based on a SCBR 214, denoted $P_0$ for the model. Continuing on, the input beam path 120 in the physical model is denoted $R_4$ for the purpose of the mathematical model; the first reflection beam path 122 is designated $R_3$; the second reflection beam path 130 is designated $R_2$; the third reflection beam path 138 is designated $R_1$; and the output reflection beam path 148 is designated $R_0$. More particularly, $R_0$ through $R_1$ represent the chief ray of a geometric optics system.

In the mathematical model there are additional parameters needed to fully characterize the system. That is, $n_1$, $n_2$, $n_3$, and $n_4$ designate unit vectors normal, respectively, to mirrors $M_1$, $M_2$, $M_3$ and $M_4$ at points of reflection $Pr_1$, $Pr_2$, $Pr_3$ and $Pr_4$ on those mirrors. $P_1$, $P_2$, $P_3$ and $P_4$ designate the center points of each mirror through which the four respective orthogonal axes of rotation 148, 134, 126 and 114 pass, respectively. The corresponding angles of rotation of each mirror about those axes are $\alpha_1$, $\alpha_2$, $\alpha_3$ and $\alpha_4$, respectively, measured from the adjacent principal axis. The separation lengths between the points $P_0$-$P_1$; $P_1$-$P_2$; $P_2$-$P_3$; and $P_3$-$P_4$ are $L_1$, $L_2$, $L_3$ and $L_4$, respectively, measured from the adjacent principal axis. Finally, $\Theta_0$ is the angle of divergence of $R_0$ from the axis $P_0$-$P_1$, and $\gamma_0$ is the angle of rotation of $R_0$ around $P_0$-$P_1$.

Accordingly, in FIG. 3 the numbers designating the physical model increase from input 212 to output 210, while the numbers designating the parameters of the mathematical model increase from output 210 to input 212. These designations, along with the items they designate, are summarized in Table 1 hereafter.

| Mathematical Model Parameter | Physical Model Designation | Description |
|---|---|---|
| $\alpha_1$ through $\alpha_4$ | | Angles of mirrors 1 through 4 measured from the adjacent principal axis |
| $L_1$ through $L_4$ | | Separation lengths along the principal axes between SCBR point and the center points of mirrors 1 through 4 |
| $M_1$ through $M_4$ | 118, 116, 114 and 112 | Mirrors 1 through 4 |
| $n_1$ through $n_4$ | | Unit vectors, normal to mirrors, at point of reflection |
| $P_0$ through $P_4$ | | P0 is the point about which synthetic beam rotation occurs. P1 through P4 define the principal set of orthogonal axes for the system |

| Mathematical Model Parameter | Physical Model Designation | Description |
|---|---|---|
| $Pr_1$ through $Pr_4$ | 148, 138, 130 and 122 | Points of reflection 1 through 4 |
| $R_0$ through $R_4$ | 148 through 120 | Segments of the chief ray through the system SCBR point to the axis of a collimated light source |
| $\theta_o$ | | Angle of divergence of $R_0$ from the axis P0-P1 |
| $\gamma_0$ | | Clocking angle of $R_0$ about the axis P0-P1 |

5. Four Mirror Control System

According to the mathematical model of a four mirror system disclosed herein, among the four variables of mirror position, $\alpha_1$ through $\alpha_4$, only $\alpha_1$ and $\alpha_2$ are fully independent variables. Their independence occurs when the other parameters of the configuration, such as the lengths between mirror centers $L_1$ through $L_4$ are fixed for a specific scanner design optimized for factors such as the location of the SCBR relative to the scanner system and the cone angle. When these parameters are fixed, the mirror positions $\alpha_1$ and $\alpha_2$ become single valued functions of the cone angle $\theta_o$ and clocking angle $\gamma_0$. The mirror angles $\alpha_3$ and $\alpha_4$ are completely determined functions of the positions of mirrors $M_1$ and $M_2$. These dependencies permit the specific control system design to be relatively simple to a person having ordinary skill in the art. Mirror angles $\alpha_3$ and $\alpha_4$ are a function of the beam angles $\theta_o$ and $\gamma_0$, and are calculated from mirror angles $\alpha_1$ and $\alpha_2$.

Figure 4:
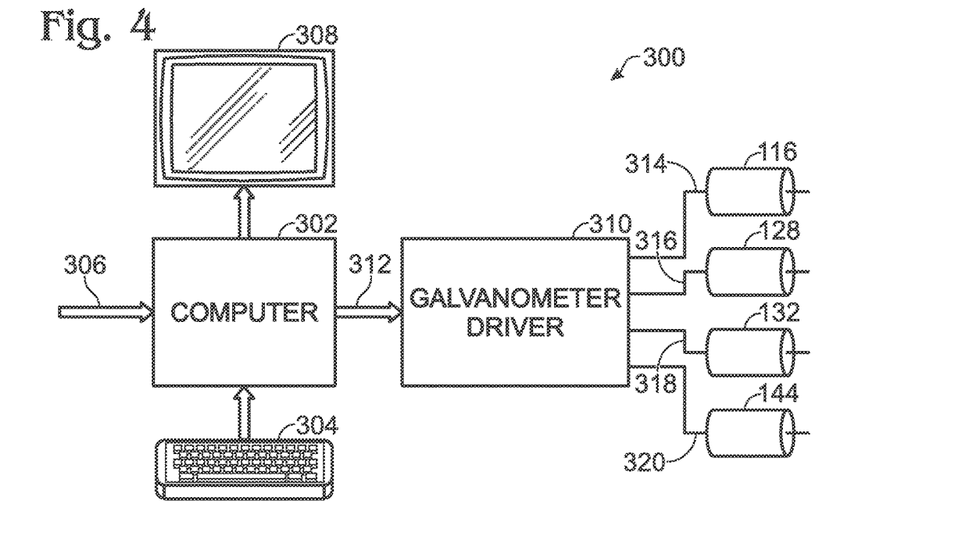
FIG. 4 is a block diagram of a control system suitable for use in a four-mirror scanning system according to the present invention.

Referring to FIG. 4, a suitable control system 300 for a four-mirror scanning system comprises a programmable digital computer 302 having a manual control input 304, a data control input 306, and a display 308. Because of the particular power signal typically required by galvanometers 116, 128, 132, and 144, a galvanometer driver 310 is provided to convert digital signals on computer output 312 to analog signals on galvanometer signal lines 314, 316, 318, and 320, respectively, as will be understood by a person having ordinary skill in the art. A suitable computer program for determining the mirror positions based on the SCBR, the scanning beam angle of divergence $\theta_0$, and the clocking beam angle $\gamma_0$ is set forth in Appendix A to this specification. The program is written in high level MathCAD 15® code, so the principles embodied in that code may be readily understood, adapted, and translated into other code suitable for a particular application by a person having ordinary skill in the art.

This code, and other code derived from this code, together with the rest of this disclosure can be used to construct a four-mirror scanner and program it according to the invention. For a three-mirror system, $M_2$ may be omitted, in which case the axes of rotation of the three remaining mirrors and control galvanometers must be at oblique angles to one another. The mathematical model disclosed herein must therefore be modified to take the oblique angles into account.

6. Double-Ended System

A double-ended scanning system with two synthetic centers of beam rotation may also be made according to the principles of the invention. If a system of three, or four, mirrors is arranged so as to be essentially symmetric in two perpendicular planes whose intersection form a central optical axis, an SCBR may be generated at each end. The loci of the SCBRs may be made selectable by software that controls the mirror galvanometers. Again, by analogy, to ray optics, synthetic "f-numbers" at each end of the system may also be selectively generated by control software. The f-numbers are only indirectly dependent on hardware. Such a double-ended optical system with SCBRs at both ends may be used to couple any two arbitrarily selected on-axis lenses with differing f-numbers.

7. Descriptions of Two Specific Four Mirror ("Quad") System

Off-The Shelf Parts

Figure 5:
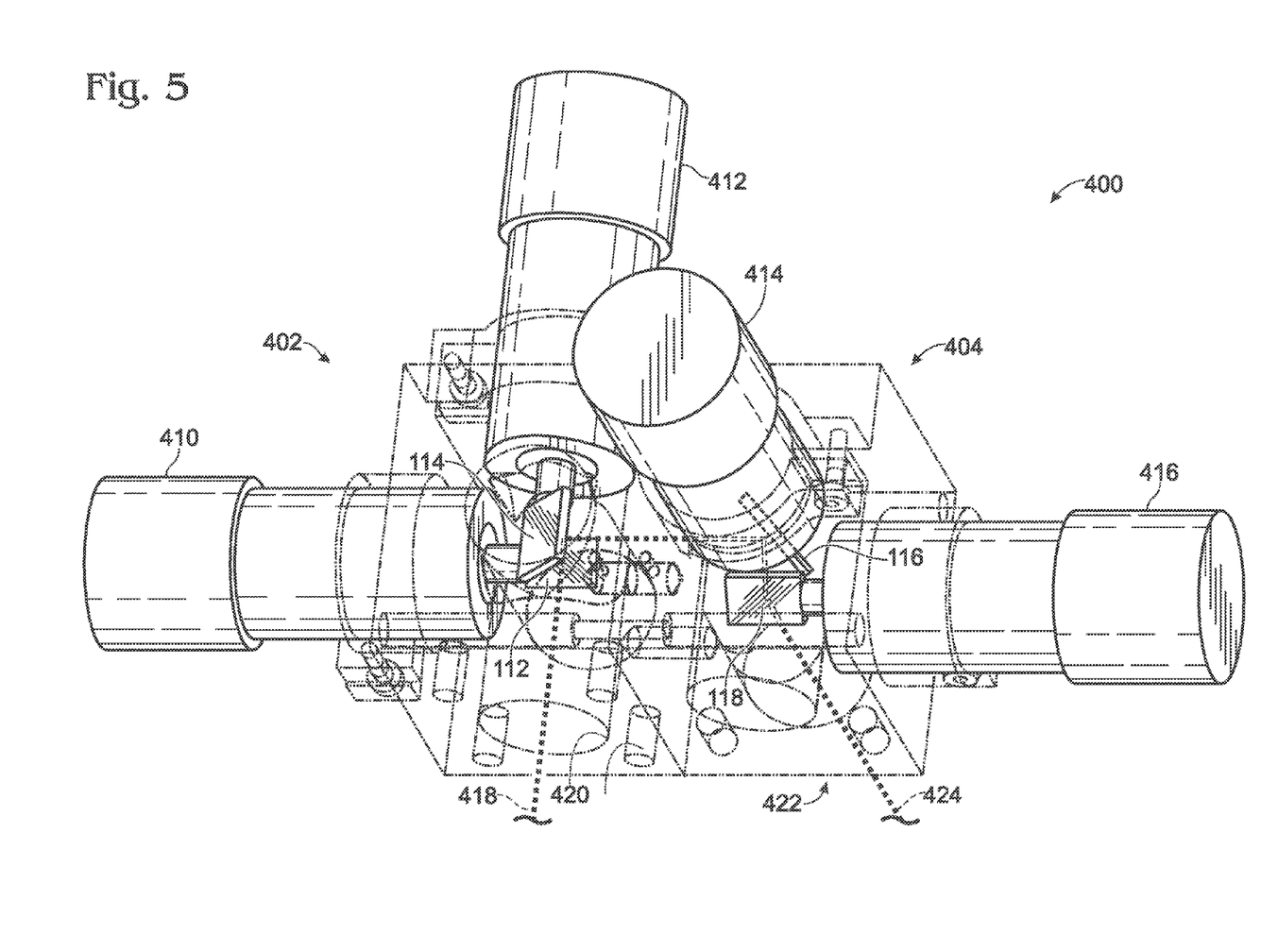
FIG. 5 is a three-dimensional rendering of an embodiment of a four-mirror scanning system including respective galvanometers to rotate the mirrors according to the present invention using off-the-shelf parts.

A basic Quad beam scanning system 400 can be assembled using two off-the-shelf galvanometer-based steering assemblies 402 and 404, as shown in FIG. 5. When attached to one another, the combined bodies 406 and 408 of the respective steering assemblies form a convenient optical bench to support four mirrors. In this system, the first mirror 112 is controlled by galvanometer 410, the second mirror 114 is controlled by galvanometer 412, the third mirror 116 is controlled by galvanometer 414, and the fourth mirror 118 is controlled by galvanometer 416. Thus, the beam 418, which enters port 420 and leaves through port 422, is caused to be directed through a selected SCBR 424 in a selected direction $\theta_0$, $\gamma_0$.

Optimized Mirror Packing

Taking the actual dimensions of available actuator components in combination with the mathematical model described above enables high mirror packing densities to be achieved when the scanning system according to the principle of the invention is integrated into an optical bench designed for a particular purpose. An advantage of a compact system can also be an increase in field of view.

Figure 6:
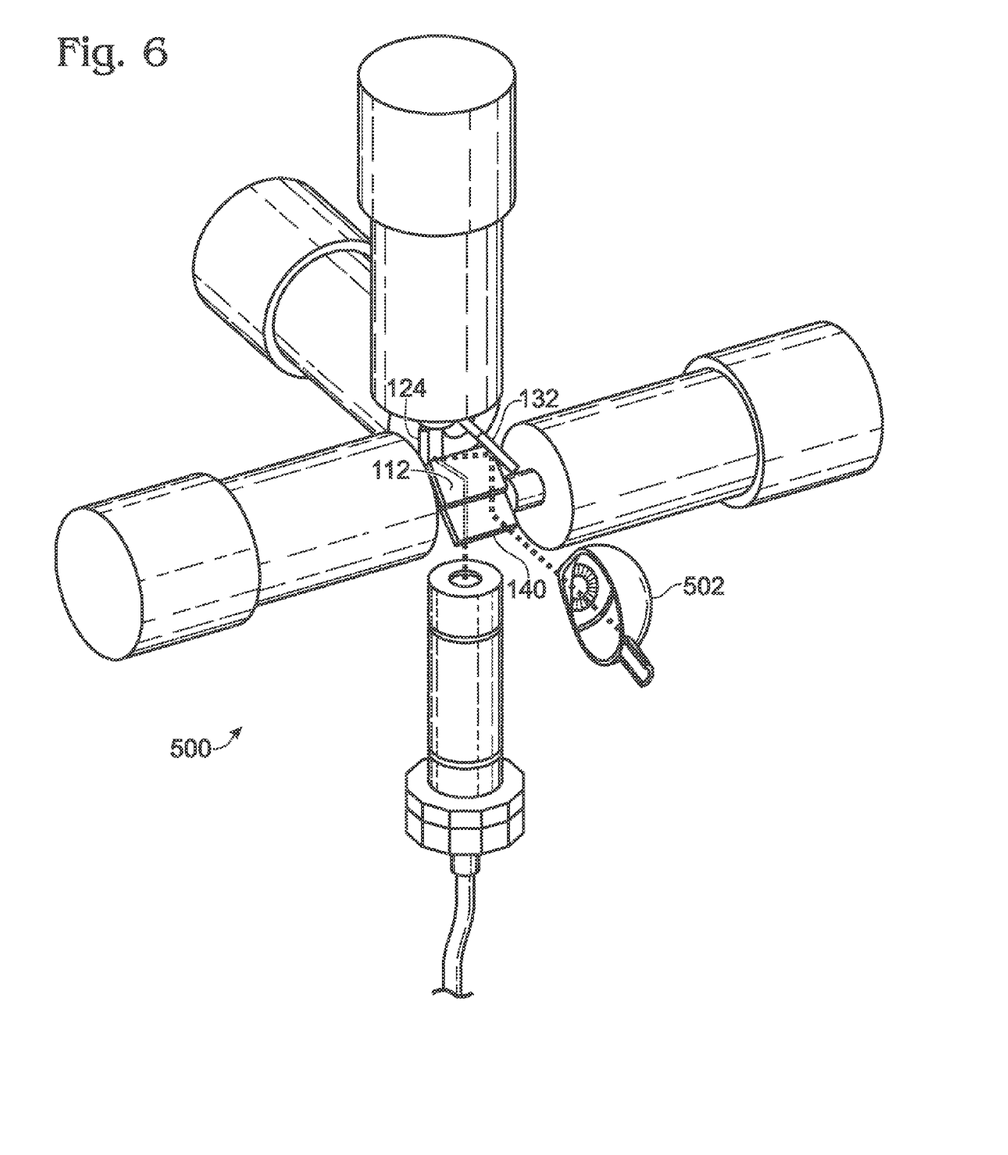
FIG. 6 is perspective of a three-dimensional rendering of a four-mirror scanning system including respective galvanometers to rotate the mirrors according to the present invention, configured to scan the retina of a human eye.
Figure 7:
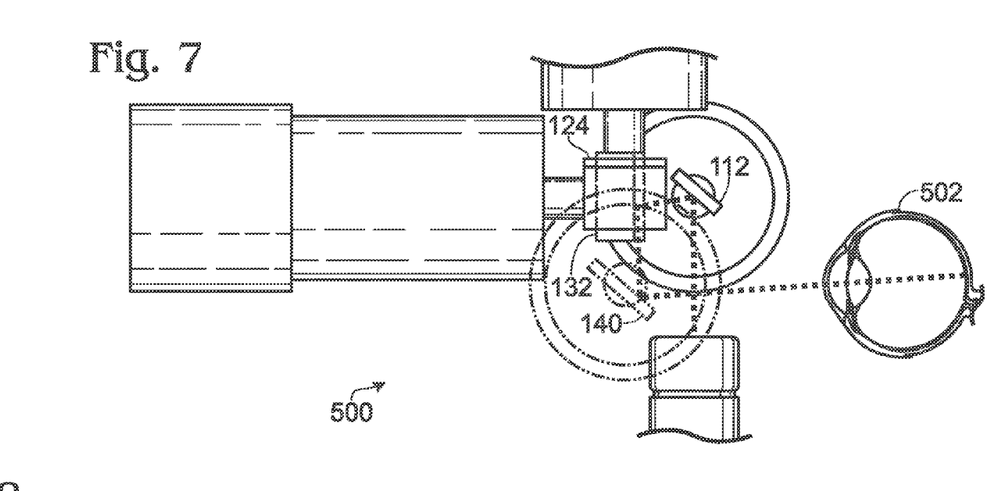
FIG. 7 is a side view of the scanning system shown in FIG. 6.

FIGS. 6 and 7 show a Quad scanning system 500 arranged for retinal scanning. The human eye 502 shown in cross-section is shown to normal adult human scale with respect to the galvanometer actuators.

Further contraction of the assembly is possible beyond that shown above. This is especially true when the travel of the galvos mirrors is limited from a normal 360 degrees of rotation, to only that motion necessary to achieve the scanning desired. When the constraint for "whole turn" rotation is lifted, the edges of mirrors may be extended into what were previous dynamic envelopes, save for unutilized ranges of motion. Constraining the "whole turn" rotation requires only the inclusion of appropriate limit stops on the mirror axes themselves along with a concurrent limitation on the range of commended motion from the controller.

Control Program Calibration

Control systems for scanning mirror assemblies are often based on the premise that axes of mirror rotation are truly orthogonal and that the mirror surfaces are identically the axes of rotation. In practice each axis will be slightly skew from an ideal coordinate reference frame. To obtain a system of the highest accuracy incorporating the tolerances of assembly into the control system is necessary. A non-contact method may be used to identify the as-built axes of a quad scanner assembly in the final configuration and these values may be entered into a "look-up" table for the control system.

The controller can then adapt to calculate each beam rotation based on the "true" rather than the "nominal" axis of each galvos mirror.

The calibration method is an iterative one. The method is one of taking the partial derivatives of the equations of the scanning beam motion with respect axis alignment; selecting cases in the range of permissible motion where the influence of one bearing axis is greater than others; approximating the axis error from that axis; inserting a corrective transformation matrix in the equation of motion, and repeating to convergence. A theodolite may be used, but in the four-mirror system according to the invention, it should ordinarily be sufficient to project the exit beam to targets located some meters distant.

11. A Retinal Scanner

Scanner Assembly

Figure 8:
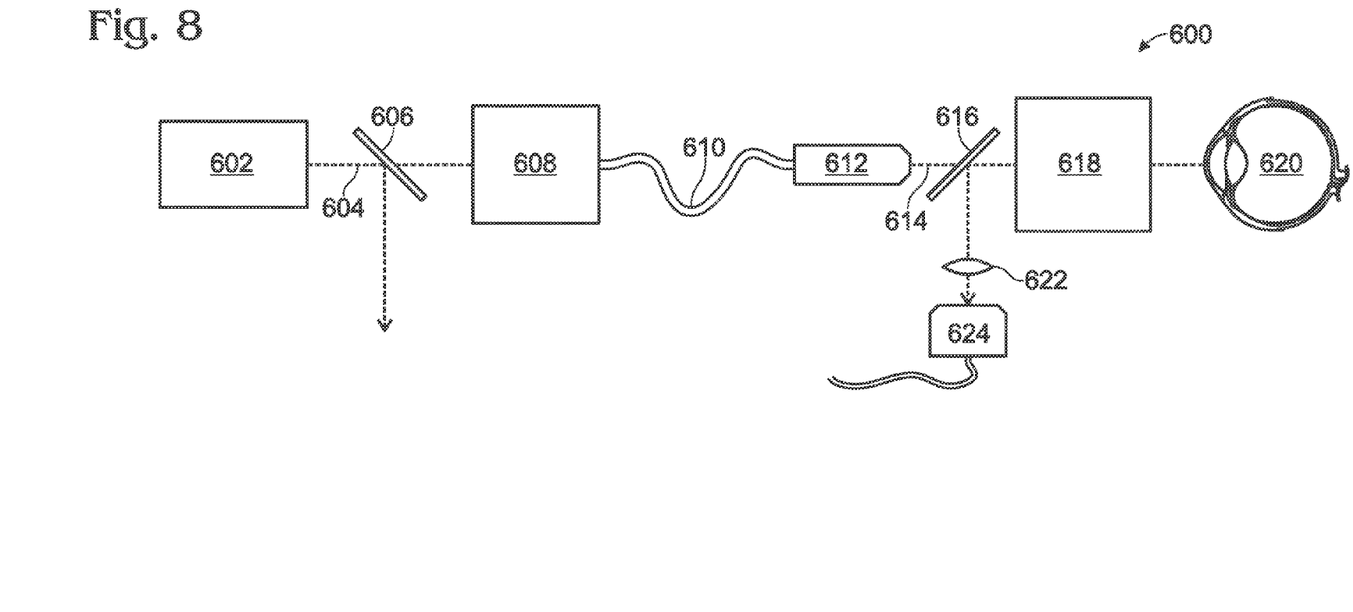
FIG. 8 is a block diagram of a retinal scanner employing a four-mirror scanning system according to the present invention.

A block diagram summarizing the incorporation of a quad scanner into the complete retinal scanner instrument 600 is shown in FIG. 8. An important feature of this instrument enabled by the quad scanner is that the scanning can be achieved with the SCBR as close as possible to the retina, that is, just outside or slightly inside the eye, to achieve a high scan angle and, thence, a more complete coverage of the entire retinal area.

In in the embodiment of FIG. 8, a broadband laser 602 produces a light beam 604 which passes through a low pass dichroic filter 606 that rejects high energy light, then through an acousto-optical tunable filter 608 so as to produce an output light beam tunable over a selected range. That output light beam is coupled by an optical fiber 610 to a collimator 612 to produce a scanning beam 614. A suitable laser may be, for example, a Fianium "WhiteLase Micro" supercontinuum laser and the system may be used to produce useful power over a range of 450 nm-1800 nm, averaging >2 nW/nm when pulsed at 40 Mhz. This laser is offered by Fianium Ltd, 20 Compass Point, Ensign Way, Southampton, SO31 4RA.

The scanning beam 614 travels through a beam splitter 616 to a quad galvos scanner 618 as described herein. The scanner is disposed so as to produce a SCBR close to or within and eye 620 so as to scan the retina within the eye. Backscattered light from the retina propagates back through the scanner 618 and reflects off the beam splitter 616 to a lens 622, which focuses that light on an amplified diode detector 624, as will be understood by a person having ordinary skill in the art.

Application of QG Retinal Scanning to Early Detection of Alzheimer's Disease

The early detection of Alzheimer's disease through the retinal monitoring of β-amyloid (Aβ) plaques, the neuropathological hallmarks of Alzheimer's disease (AD), presents an opportunity for use of the present invention. Images designated b and b' in Koronyo-Hamaoui M, Koronyo Y, Ljubimov A V, Miller C A, Ko M K, Black K L, Schwartz M, Farkas D L, "Identification of amyloid plaques in retinas from Alzheimer's patients and noninvasive in vivo optical imaging of retinal plaques in a mouse model." *Neuroimage*, 2011, January; 54 Suppl 1:S204-17 Epub 2010 Jun. 13, show the relatively high contrast of this signal, which comes from the curcumin (from the culinary spice turmeric ginger family Zingiberaceae) label that attaches itself very specifically to the plaques. Its florescence is in the visible range, detectable with current imaging technologies. The full paper was published at http://www.ncbi.nlm.nih.gov/pmc/articles/PMC2991559/.

A further extension of this imaging would allow the (significantly weaker, visible wavelength) autofluorescence of β-amyloid (Aβ) plaques to report on their whereabouts, features and dynamics.

The terms and expressions which have been employed in the foregoing specification are used therein as terms of description and not of limitation, and there is no intention, in the use of such terms and expressions, to exclude equivalents of the features shown and described or portions thereof it being recognized that the scope of the invention is defined and limited only by the claims that follow.

The invention claimed is:

1. An optical beam scanning system for scanning the retina of an eye, comprising:

a front mirror having a motor to orient the front mirror relative to a frame of reference so as to receive and redirect an optical beam in accordance with the orientation of the front mirror;

a primary intermediate mirror having a motor to orient the primary intermediate mirror relative to the frame of reference so as to receive and redirect the optical beam in accordance with the orientation of the primary intermediate mirror;

a back mirror having a motor to orient the back mirror relative to the frame of reference so as to receive and redirect the optical beam in accordance with the orientation of the back mirror; and a controller connected to the front, primary intermediate and back mirrors to orient the front, primary intermediate and back mirrors so that the optical beam received by the front mirror from a given direction is redirected toward the primary intermediate mirror, and is redirected by the primary intermediate mirror toward the back mirror, and is redirected by the back mirror so as to pass through a selected point spaced apart from the back mirror in one of a plurality of selectable different directions such that the optical beam exiting the back mirror rotates about a synthetic center of beam rotation (SCBR), the SCBR being not located at a surface of any of the front mirror, the primary intermediate mirror, or the back mirror.

2. The beam scanning system of claim 1, wherein each front mirror, the intermediate mirror and the back mirror has a respective axis of rotation, the axes of rotation of the front, intermediate and back mirrors being non-parallel to one another.

3. The beam scanning system of claim 2, wherein each of the front mirror motor, the intermediate mirror motor and the back mirror motor have axes of rotation collinear with their respective mirrors.

4. The beam scanning system of claim 3, wherein at least one of the mirrors has a planar reflective surface and an axis of rotation essentially coplanar with that reflective surface.

5. The beam scanning system of claim 1, further comprising a secondary intermediate mirror having a motor to orient the secondary intermediate mirror relative to the frame of reference so as to receive and redirect the optical beam in accordance with the orientation of the secondary intermediate mirror in response to the control system, the secondary intermediate mirror being disposed between the primary intermediate mirror and the back mirror so as to receive the beam from the primary intermediate mirror and redirect it toward the back mirror, the beam being redirected by the primary intermediate mirror toward the back mirror off of the secondary intermediate mirror.

6. The beam scanning system of claim 5, wherein three of the front mirror, the primary intermediate mirror, the secondary intermediate mirror and the back mirror have respective axes of rotation that are essentially perpendicular to one another, and two of the front mirror, the primary intermediate mirror, the secondary intermediate mirror and the back mirror have axes of rotation that are essentially parallel to one another.

7. The beam scanning system of claim 1, wherein the controller comprises a digital computer programmed to determine coordinates of the SCBR and a beam direction through the SCBR, determine a corresponding angle for the front mirror, the primary intermediate mirror, or the back mirror, and provide signals to the corresponding mirror motor to place the front mirror, the primary intermediate mirror, or the back mirror at the corresponding angle.

8. A method of controlling an optical beam for scanning the retina of an eye, comprising:
   arranging a system of at least three mirrors having respective axes of rotation parallel to a tangent to the respective mirror surfaces; and
   rotating the mirrors so that the beam is redirected by a first of the mirrors to a second of the mirrors, by the second of the mirrors to a third of the mirrors, and by the third of the mirrors in a selected direction such that the optical beam exiting the third of the mirrors rotates about a synthetic center of beam rotation (SCBR), the SCBR being not located at a surface of any of the mirrors.

9. The method of claim 8, further comprising arranging a fourth mirror arranged between the second of the mirrors and the third of the mirrors to redirect the beam from the second of the mirrors to the fourth mirror, and to redirect the beam from the fourth mirror to the third of the mirrors.

10. The beam scanning system of claim 1, wherein the SCBR is placed at a front focal point of an objective lens.

11. The method of claim 8, wherein the SCBR is placed at a front focal point of an objective lens.

12. The method of claim 8, further comprising scanning the retina of the eye without a scan lens.

\* \* \* \* \*